(12) United States Patent
Mitchell et al.

(10) Patent No.: US 9,629,954 B2
(45) Date of Patent: Apr. 25, 2017

(54) TUBE PASSAGE SEALING SYSTEM

(71) Applicant: beteSTRONGCASES, LLC, Northfield, IL (US)

(72) Inventors: Connor F. Mitchell, Skokie, IL (US); Patrick M. Harris, Downers Grove, IL (US)

(73) Assignee: beteSTRONGCASES, LLC, Northfield, IL (US)

( * ) Notice: Subject to any disclaimer, the term of this patent is extended or adjusted under 35 U.S.C. 154(b) by 80 days.

(21) Appl. No.: 14/704,637

(22) Filed: May 5, 2015

(65) Prior Publication Data
US 2016/0325888 A1    Nov. 10, 2016

(51) Int. Cl.
| | | |
|---|---|---|
| *F16J 15/02* | (2006.01) | |
| *F16J 15/06* | (2006.01) | |
| *A61J 1/00* | (2006.01) | |
| *A61M 5/14* | (2006.01) | |
| *A61M 5/142* | (2006.01) | |
| *B29C 65/00* | (2006.01) | |

(52) U.S. Cl.
CPC .............. *A61M 5/14* (2013.01); *A61J 1/00* (2013.01); *A61M 5/14244* (2013.01); *B29C 65/00* (2013.01); *B29C 66/00* (2013.01); *F16J 15/024* (2013.01); *A61M 2205/502* (2013.01); *A61M 2205/505* (2013.01); *A61M 2205/507* (2013.01); *F16J 15/022* (2013.01); *F16J 15/061* (2013.01)

(58) Field of Classification Search
CPC ........ F16J 15/021; F16J 15/024; F16J 15/025; F16J 15/061; F16J 15/104; H02G 15/013; H02G 15/10; H02G 15/113; H02G 3/08; H02G 3/081; H02G 3/083; H02G 3/088; A61J 1/00; F16L 5/02
See application file for complete search history.

(56) References Cited

U.S. PATENT DOCUMENTS

| | | | | |
|---|---|---|---|---|
| 4,524,805 A | * | 6/1985 | Hoffman | F16K 15/147 137/846 |
| 5,017,153 A | | 5/1991 | Bowman | |
| 5,330,437 A | * | 7/1994 | Durman | A61M 39/06 137/846 |
| 5,347,084 A | * | 9/1994 | Roney | G02B 6/4447 174/92 |
| 5,351,973 A | | 10/1994 | Taniuchi | |
| 5,482,299 A | | 1/1996 | Saito | |

(Continued)

*Primary Examiner* — Nicholas L Foster
(74) *Attorney, Agent, or Firm* — Neustel Law Offices; Michael S. Neustel

(57) ABSTRACT

A tube passage sealing system for allowing passage of a tube from the interior to the exterior of a case such that the case is sealed against fluid intrusion whether a tube is present or absent. The tube passage sealing system generally includes a case having a first portion and a hingedly connected second portion. The portions may be closed together to define a compartment in which a device may be positioned. A tube seal assembly is included which allows a tube leading from the device within the compartment to exit the case through a passage formed in the assembly. The tube seal assembly generally includes a first tube seal and second tube seal which combine when the case is closed to seal around the tube. Some embodiments may include blocking portions on the tube seals which will act to seal the passage when a tube is not present.

12 Claims, 25 Drawing Sheets

(56) References Cited

U.S. PATENT DOCUMENTS

| | | | | |
|---|---|---|---|---|
| 5,561,269 | A | * | 10/1996 | Robertson ................ H01R 4/70 174/92 |
| 5,675,124 | A | | 10/1997 | Stough |
| 6,029,981 | A | * | 2/2000 | Hawley .................... F16L 5/10 277/607 |
| 6,099,340 | A | * | 8/2000 | Florentine .......... H01R 13/6392 439/367 |
| 6,497,346 | B1 | | 12/2002 | Dubois |
| 6,862,852 | B1 | | 3/2005 | Beele |
| 7,484,973 | B2 | | 2/2009 | Westhoff |
| 8,141,587 | B2 | | 3/2012 | Doig |
| 8,241,251 | B2 | | 8/2012 | Gresham |
| 8,448,799 | B2 | | 5/2013 | Thurman |
| D693,114 | S | * | 11/2013 | Lemanski, Sr. ............. D3/203.8 |
| 2008/0169116 | A1 | * | 7/2008 | Mullaney ............ G02B 6/4471 174/92 |
| 2009/0058018 | A1 | * | 3/2009 | Mullaney ............ G02B 6/4447 277/625 |
| 2010/0006314 | A1 | * | 1/2010 | Wilson, II ............ H04R 1/1091 174/50.5 |
| 2016/0218468 | A1 | * | 7/2016 | Casale ................ H02G 3/0675 |

* cited by examiner

TUBE PASSAGE SEALING SYSTEM

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

Field of the Invention

The present invention relates generally to a sealing system and more specifically it relates to a tube passage sealing system for allowing passage of a tube from the interior to the exterior of a case such that the case is sealed against leakage whether a tube is present or absent.

Description of the Related Art

Any discussion of the related art throughout the specification should in no way be considered as an admission that such related art is widely known or forms part of common general knowledge in the field.

It is often desirable to store or position a fluidic device within a case. The case will prevent the fluids within the device from spilling and potentially contaminating an area or creating hazardous conditions in the case of device failure or damage. In a typical prior art case, the sealing element is a free gasket or seal which is clamped between the two case halves. In some prior art, the free gasket or seal is instead bonded to one of the case halves.

When sealing against a round tube, this one-element seal prior art configuration does not function due to the inability of the hard case section to deform enough to seal against the tube. Where two matching and opposing sealing elements are utilized to provide a channel for the tube to pass through, leakage may occur when the tube is not present between the sealing elements and thus create the risk of exposure if the fluidic device within the case becomes ruptured or otherwise compromised or ingress through the tube passage if the exterior of the case is immersed in or exposed to liquid.

Because of the inherent problems with the related art, there is a need for a new and improved tube passage sealing system for allowing passage of a tube from the interior to the exterior of a case such that the case is sealed against leakage whether a tube is present or absent.

BRIEF SUMMARY OF THE INVENTION

The invention generally relates to a tube seal system which includes a case having a first portion and a second portion hingedly connected to the first portion. The first portion and second portion may be closed together to define a compartment in which a device may be positioned. A tube seal assembly is included which will allow a tube leading from the device within the compartment to exit the case through a passage formed in the tube seal assembly. The tube seal assembly generally includes a first tube seal and second tube seal which combine when the case is closed to seal around the tube. Some embodiments may include blocking portions on the tube seals which will act to seal the passage when a tube is not present.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Figure 1:
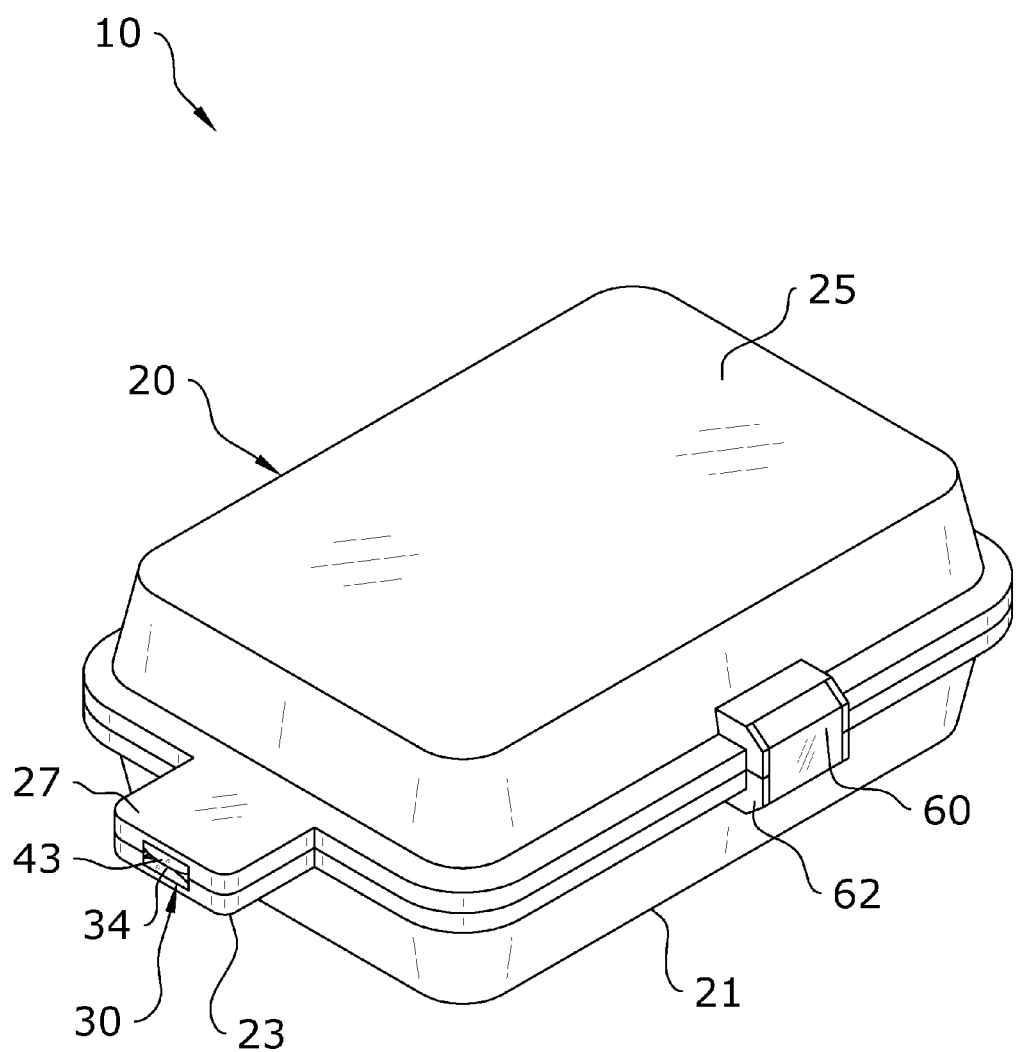
FIG. 1 is an upper perspective view of the present invention with the case closed.

Turning now descriptively to the drawings, in which similar reference characters denote similar elements throughout the several views, FIGS. 1 through 24 illustrate a tube passage sealing system 10, which comprises a case 20 having a first portion 21 and a second portion 25 hingedly connected to the first portion 21. The first portion 21 and second portion 25 may be closed together to define a compartment 24 in which a fluidic device 12 may be positioned. A tube seal assembly 30 is included which will allow a tube 13 leading from the fluidic device 12 within the compartment 24 to exit the case 20 through a passage 48 formed in the tube seal assembly 30. The tube seal assembly 30 generally includes a first tube seal 31 and second tube seal 40 which combine when the case 20 is closed to seal around the tube 13. Some embodiments may include blocking portions 35, 44 on the tube seals 31, 40 which will act to seal the passage 48 when a tube 13 is not present.

It should be noted that the present invention may be utilized with a wide range of devices, such as medical equipment, networking equipment, electrical devices, pumps, meters, sampling valves, and the like. While a focus is on fluidic devices 12, any type of device which includes a conduit or tube 13 may be utilized in combination with the present invention to protect the device from fluid intrusion.

For example, medical equipment could include infusion pumps, peristaltic pumps, monitors, and electrical stimulus devices. Networking equipment could include routers, switches and the like. Electrical devices could include electrical relays, programmable logic controllers, timers, and the like. The figures and description herein should thus not be construed as limiting usage of the present invention to fluidic devices 12.

B. Case

As shown throughout the figures, the present invention generally comprises a case 20 having a first portion 21 and a second portion 25 which close to form a compartment 24 adapted to sealably store and retain a fluidic device 12 therein. The case 20 generally has an open state in which its compartment 24 is accessible to place a fluidic device 12 therein. The case 20 also has a closed state in which the first and second portions 21, 25 are closed against each other. When in a closed state, the compartment 24 is sealed so as to prevent escape of any fluids from the fluidic device 12 and to prevent ingress of fluids into compartment 24.

The first portion 21 and second portion 25 are preferably hingedly secured to each other via a hinge 28 as shown in the figures, though it is appreciated that other configurations may be utilized to position the case 20 between its open state and its closed state. The present invention should not be construed as limited to hinged configurations. For example, one embodiment may include completely separable first and second portions 21, 25.

The case 20 may be comprised of any variety of shapes, sizes and configurations to accommodate a wide range of fluidic devices 12. While the figures illustrate the case 20 as being generally rectangular in shape, it should be appreciated that the case 20 could be any number of shapes, including round, triangular, polygonal and the like. Larger cases 20 may be provided for larger fluidic devices 12 and smaller cases 20 may be provided for more compact fluidic devices 12.

The case 20 may include a handle as shown or in some embodiments may omit a handle entirely. In some embodiments, the case 20 may include a lock to prevent unauthorized access to the fluidic device 12 stored therein. The case 20 may also include a clasp, buckle, connector, fastener, or other devices to removably or lockably secure the first and second portions 21, 25 together to seal the compartment 24.

Figure 2:
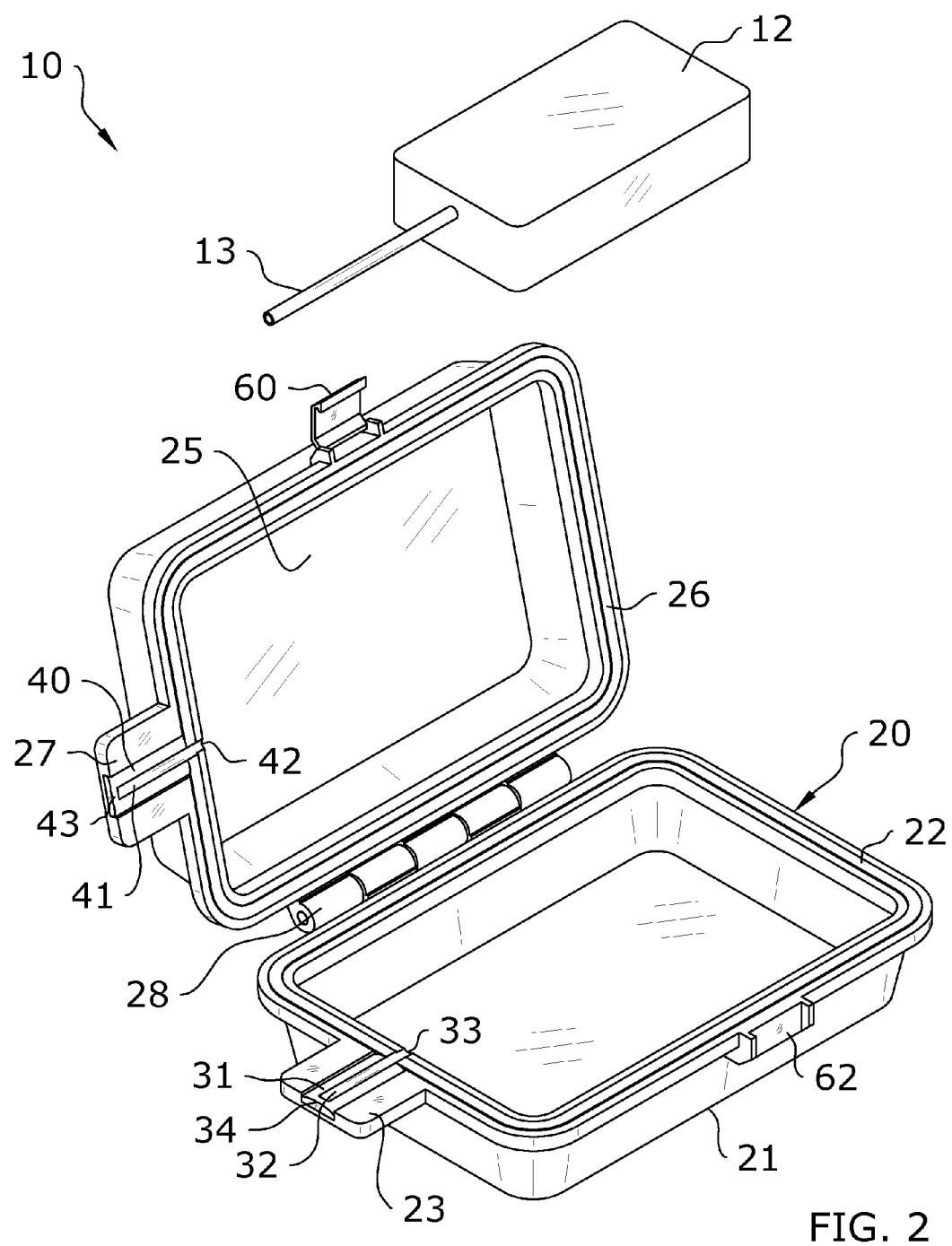
FIG. 2 is an upper perspective view of the present invention with the case opened and a fluidic device aligned for insertion with the case.

The figures illustrate a clasp 60 and clasp anchor 62 being used to removably secure the first portion 21 to the second portion 25 to close the case 20. As best shown in FIG. 2, a clasp 60 is positioned on the second portion 25 of the case 20 and a corresponding clasp anchor 62 is positioned on the first portion 21 of the case 20. When the case 20 is closed, the clasp 60 may removably engage with the clasp anchor 62 to secure the case 20 in its closed position.

Figure 23:
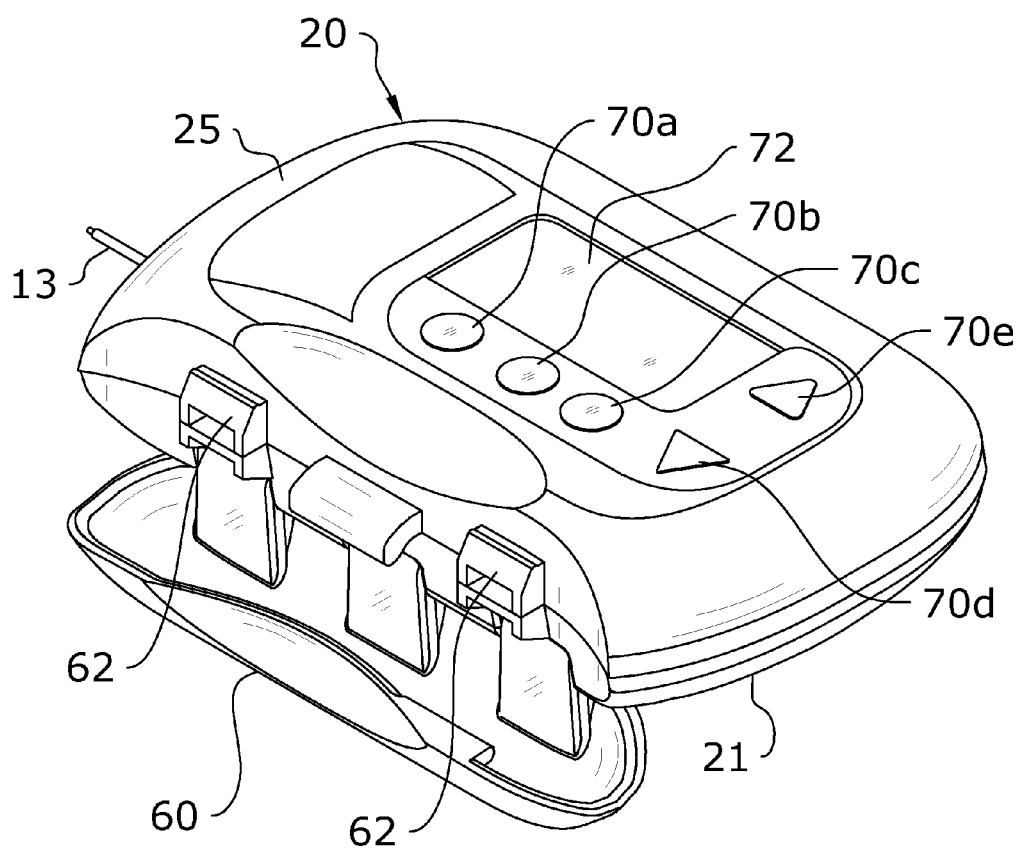
FIG. 23 is an upper perspective view of an alternate embodiment of the present invention with its clasp opened.
Figure 24:
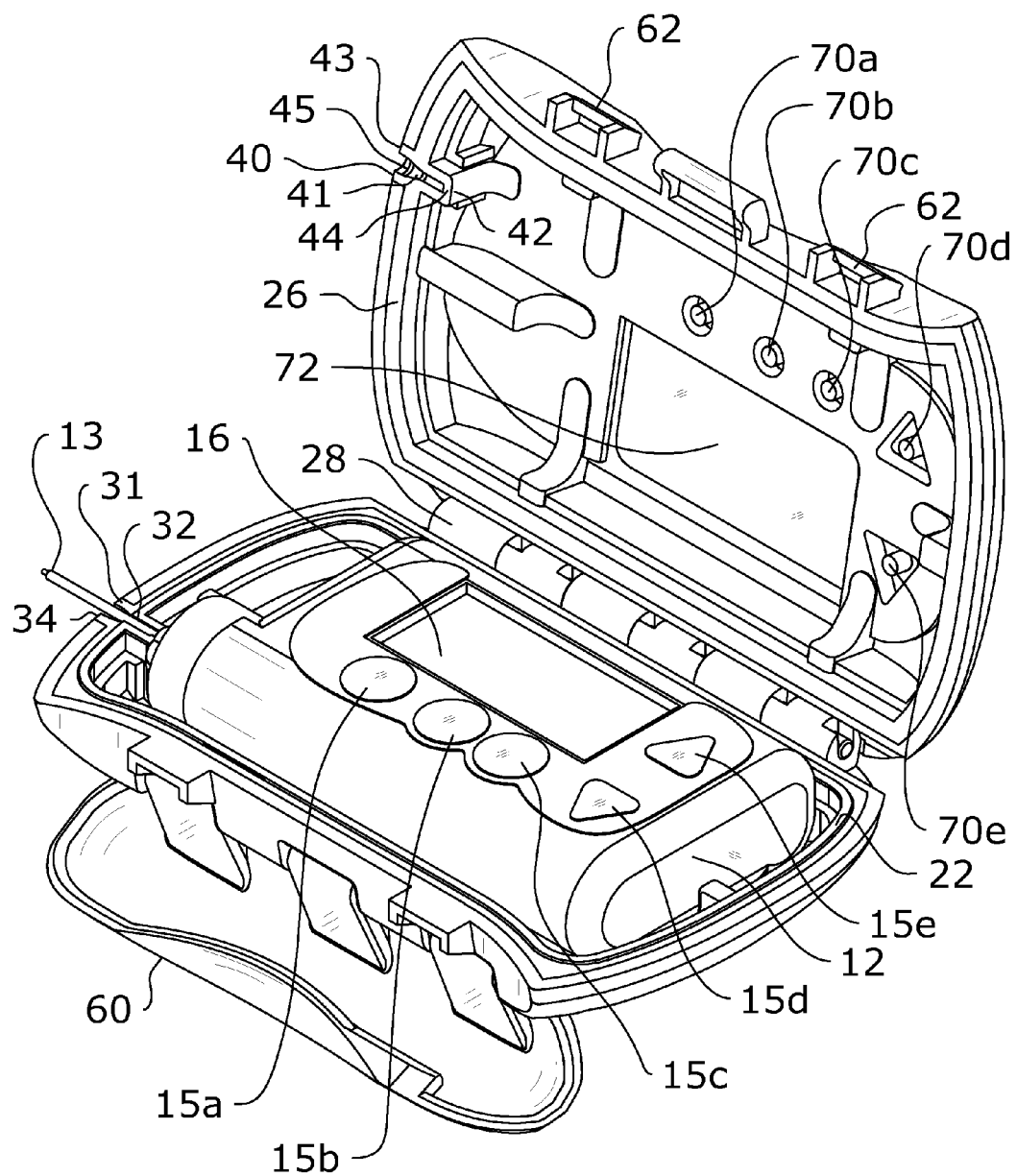
FIG. 24 is an upper perspective view of an alternate embodiment of the present invention in an opened state with a device installed.

It should be appreciated that any method or device known in the art for removably securing a first portion 21 to a second portion 25 of a case 20 may be utilized. For example, FIGS. 23 and 24 illustrate a more complex clasp 60 on the first portion 21 of the case 20 and a clasp anchor 62 on the second portion 25 of the case 20.

The first portion 21 and second portion 25 are preferably similar in shape and size so as to form a tight seal against each other when closed. In a preferred embodiment as shown in FIG. 2, the first portion 21 will include a first perimeter seal 22 along its inner perimeter and the second portion 25 will include a second perimeter seal 26 along its inner perimeter.

The perimeter seals 22, 26 may vary in construction, but will generally be comprised of a sealing material such as rubber or the like which extends around the inner perimeter of the first portion 21 and second portion 25 of the case 20. When the case 20 is in its closed state, the first perimeter seal 22 will press and seal against the second perimeter seal 26. The perimeter seals 22, 26 may be transparent or partially transparent in some embodiments.

The perimeter seals 22, 26 will act to press against each other in a manner which fully seals the compartment 24 of the case 20 when the case 20 is closed by engaging the first portion 21 with the second portion 25. Thus, fluids will be prevented from entering the compartment 24 via ingress between the first and second portions 21, 25.

Main embodiments shown in the figures utilize a two-element seal system for both the tube seal assembly 30 and the perimeter seals 22, 26 (i.e., the first and second tube seals 31, 40 and the perimeter seals 22, 26 each have two elements). While this is a preferred embodiment, it may add unwanted expense or complexity to the present invention. A partial two-element seal may thus have cost and simplicity advantages to the full two-element seals shown in main embodiments.

Figure 19:
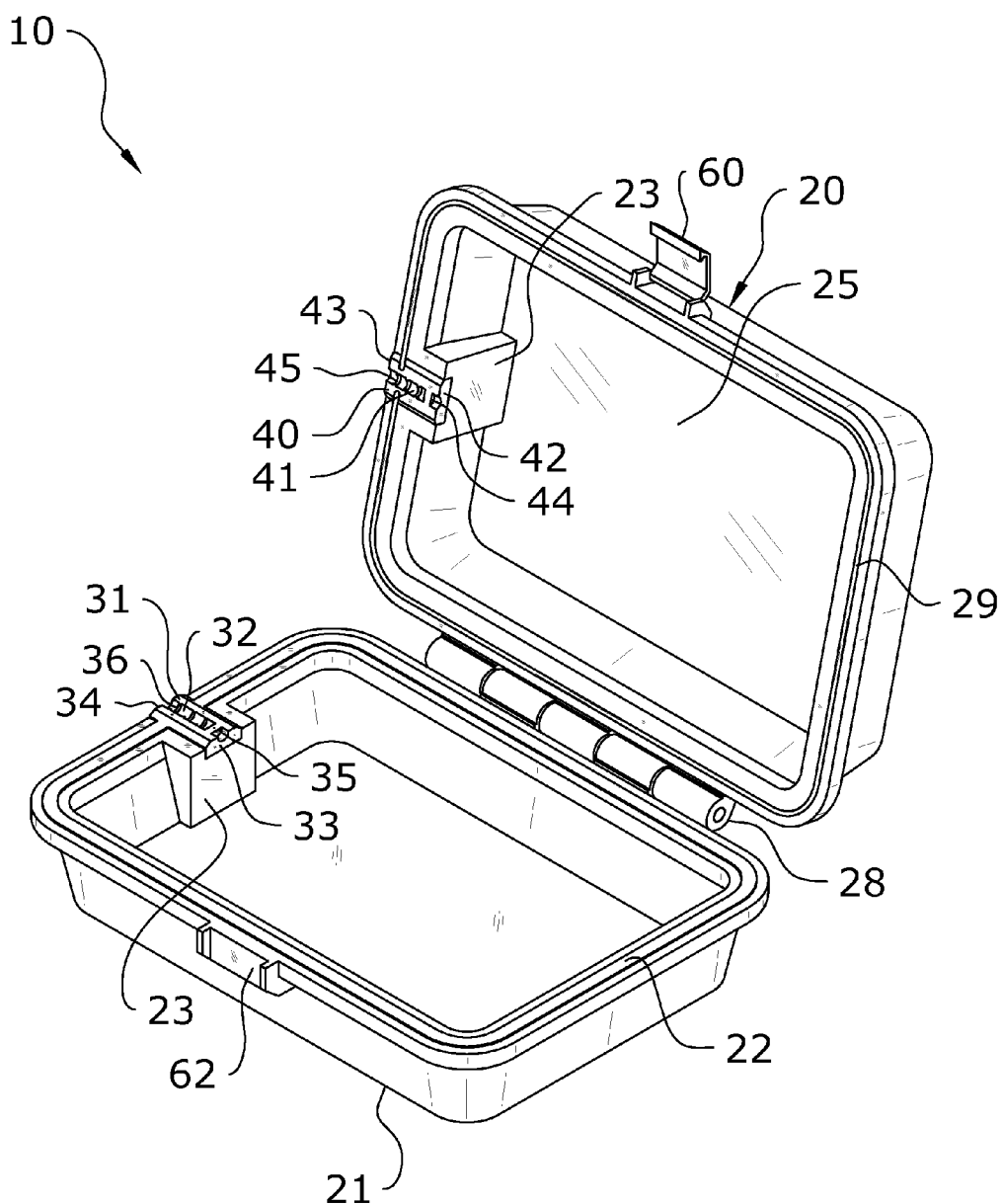
FIG. 19 is an upper perspective view of an alternate embodiment of the present invention in which a perimeter engagement member is used on the second portion of the case.
Figure 20:
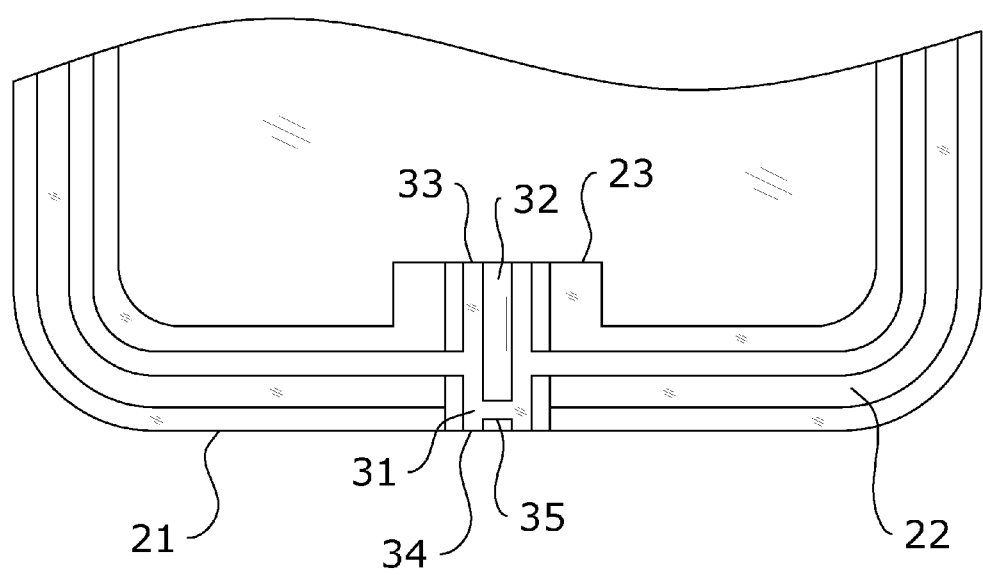
FIG. 20 is a top cutaway view of a third embodiment of the tube seal of the present invention.
Figure 21:
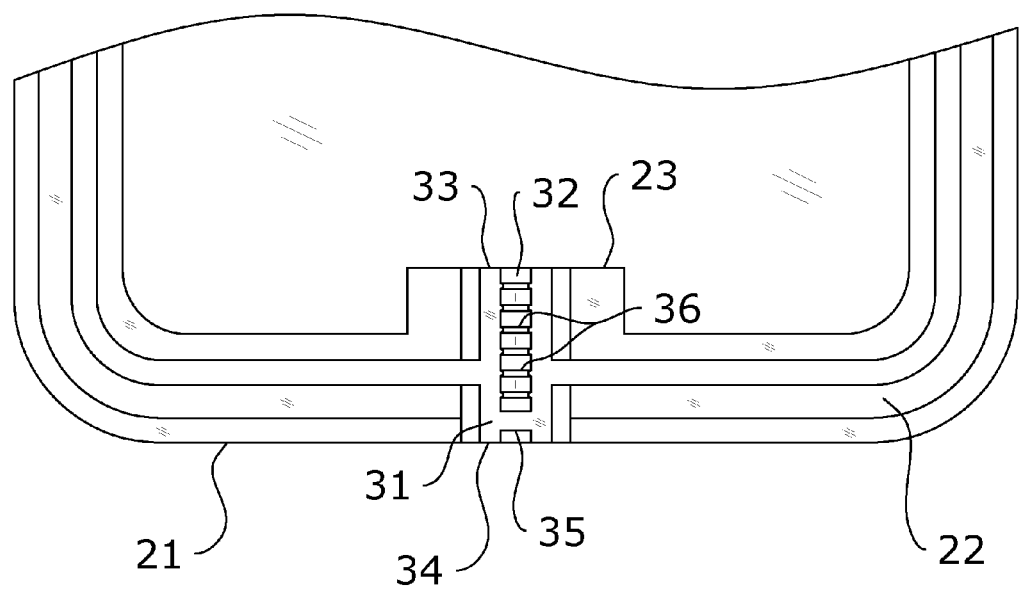
FIG. 21 is a top cutaway view of a third embodiment of the tube seal of the present invention with ribs.

FIG. 19 illustrates an alternate embodiment of the present invention in which only one perimeter seal 22 is utilized. A majority of the perimeter of the case 20 is sealed by a traditional single element seal and only in the area of the passage 48 for the tube 13 is a two-element seal utilized. In this embodiment, the first portion 21 of the case 20 includes a first perimeter seal 22 as with the main embodiment. However, the second portion 25 of the case 20 includes a perimeter engagement member 29 instead of a second perimeter seal 26.

The perimeter engagement member 29 is comprised of a raised protrusion which extends around the outer perimeter of the second portion 25 of the case 20 and which engages with and indents the first perimeter seal 22 of the first portion 21 to effectuate a seal of the majority of the perimeter of the case 20. As the seal 22 gets near the tube assembly 30, the second tube seal 40 of the second portion 25 of the case 20 overlaps the perimeter engagement member 29 to ensure sealing at the transition between the perimeter seal 22 and the tube seal assembly 30. It should be appreciated that, in other embodiments, the perimeter engagement member 29 may be included on the first portion 21 of the case 20 and used in combination with a second perimeter seal 26 on the second portion 25 instead.

Figure 22:
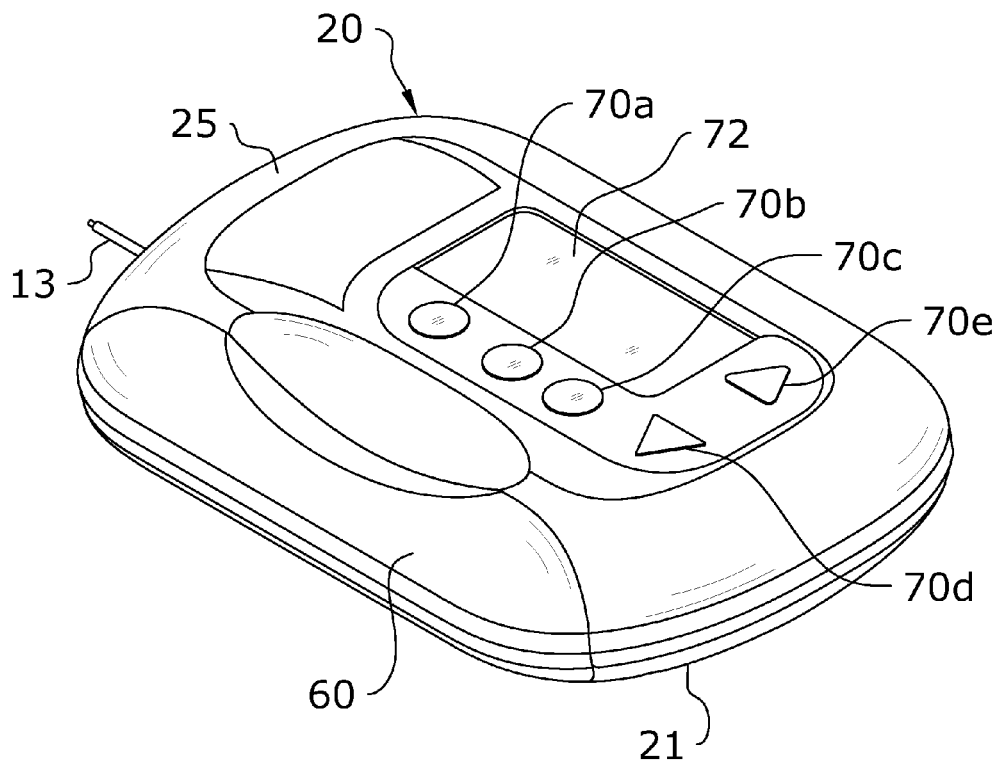
FIG. 22 is an upper perspective view of an alternate embodiment of the present invention in a closed state.

As noted, the structure of the case 20 may vary in different embodiments. FIGS. 22-24 illustrate an alternate embodiment of the case 20 which is adapted to include pass-through controls 70a-e to allow control of the device controls 15a-e of the fluidic device 12. For example, a first pass-through control 70a of the case 20 will be positioned directly above a corresponding device control 15a such that pressing down on the control 70a on the case 20 will cause the underlying device control 15a to be depressed.

The number, orientation, and positioning of the controls 70a-e may vary in different embodiments and should not be construed as limited by the exemplary figures. The alternate embodiment of the case 20 may also include a window 72 which allows a user to view the device display 16 of the fluidic device 12 when the case 20 is closed.

C. Tube Seal Assembly

The present invention is adapted to allow the tube 13 of a fluidic device 12 stored within the compartment 24 of the case 20 to exit the case 20 in a manner which seals the compartment 24 whether the tube 13 is present or absent. To provide such a feature, the present invention includes a tube seal assembly 30 which is shown throughout the figures and generally comprises a first tube seal 31 on the first portion 21 of the case 20 and a second tube seal 40 on the second portion 25 of the case 20.

Figure 6:
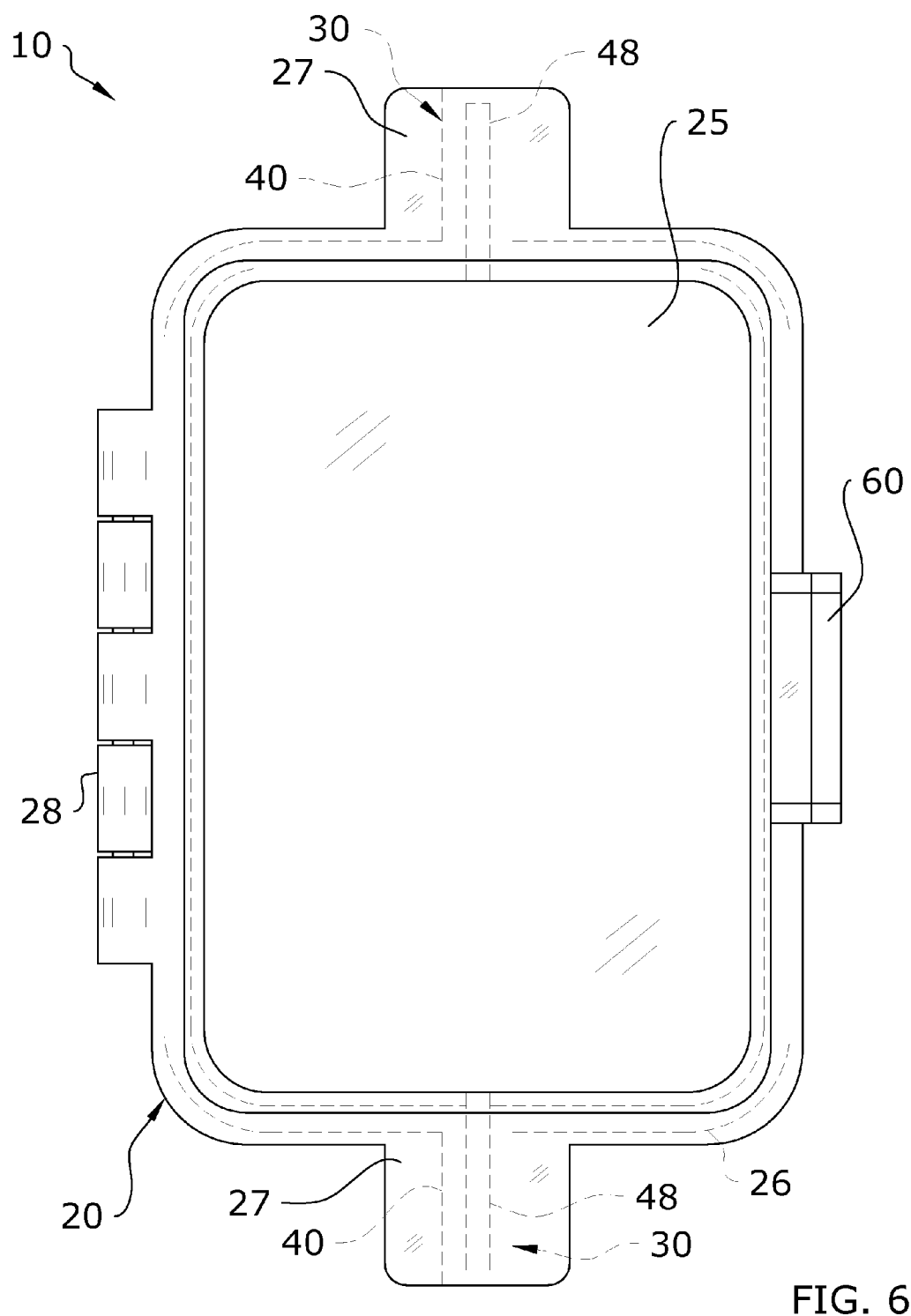
FIG. 6 is a top view of an embodiment of the case which includes a pair of tube seals to accommodate a pair of tubes.
Figure 7:
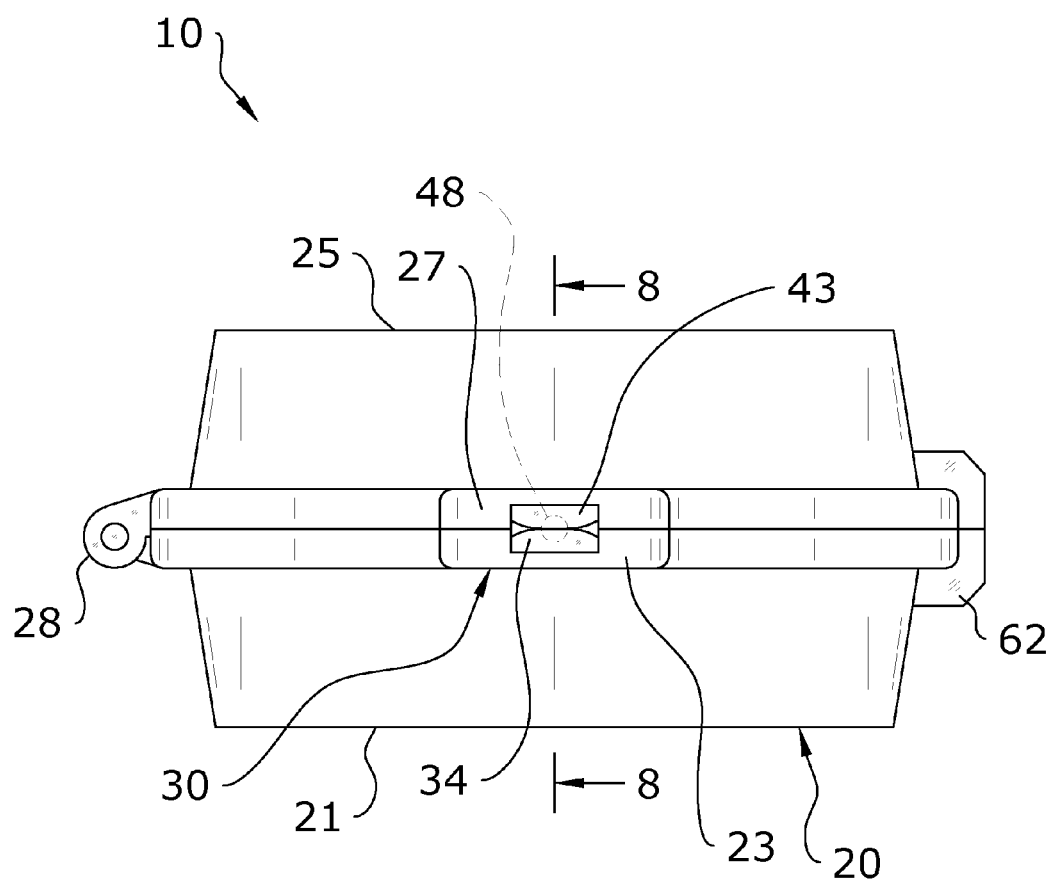
FIG. 7 is a frontal view of the case of the present invention in a closed position without a fluidic device positioned therein.
Figure 8:
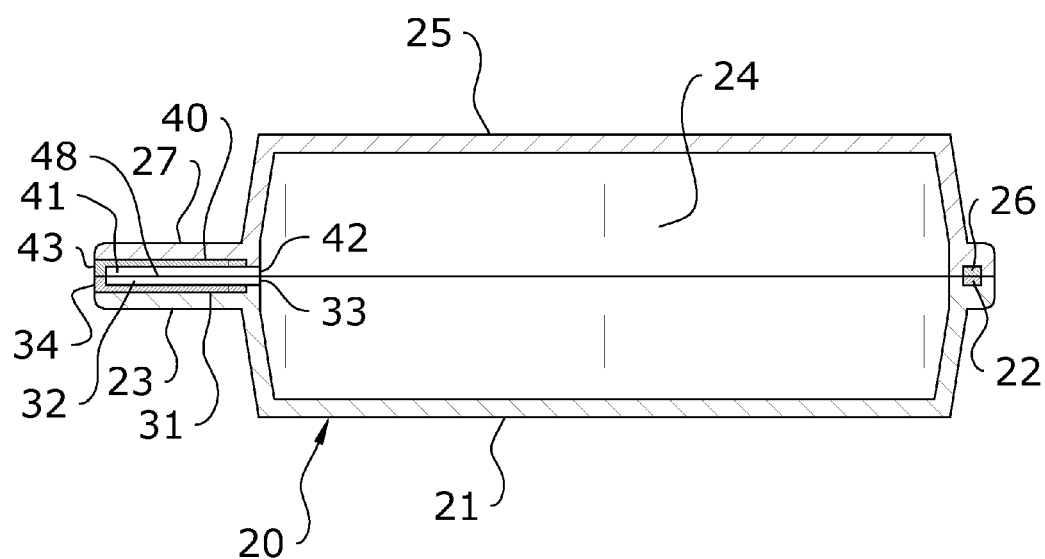
FIG. 8 is a sectional view taken along line 8-8 of FIG. 6.

In some embodiments such as shown in FIG. 6, the case 20 may include multiple tube seal assemblies 30. For example, such an embodiment may be utilized with certain electrical devices such as probes which may include two or more tubes 13, such as a power cord and a measuring probe. Other embodiments, such as a case 20 adapted for use with a router, may include tube seal assemblies 30 to accommodate multiple tubes 13 entering or exiting the case 20.

Figure 3:
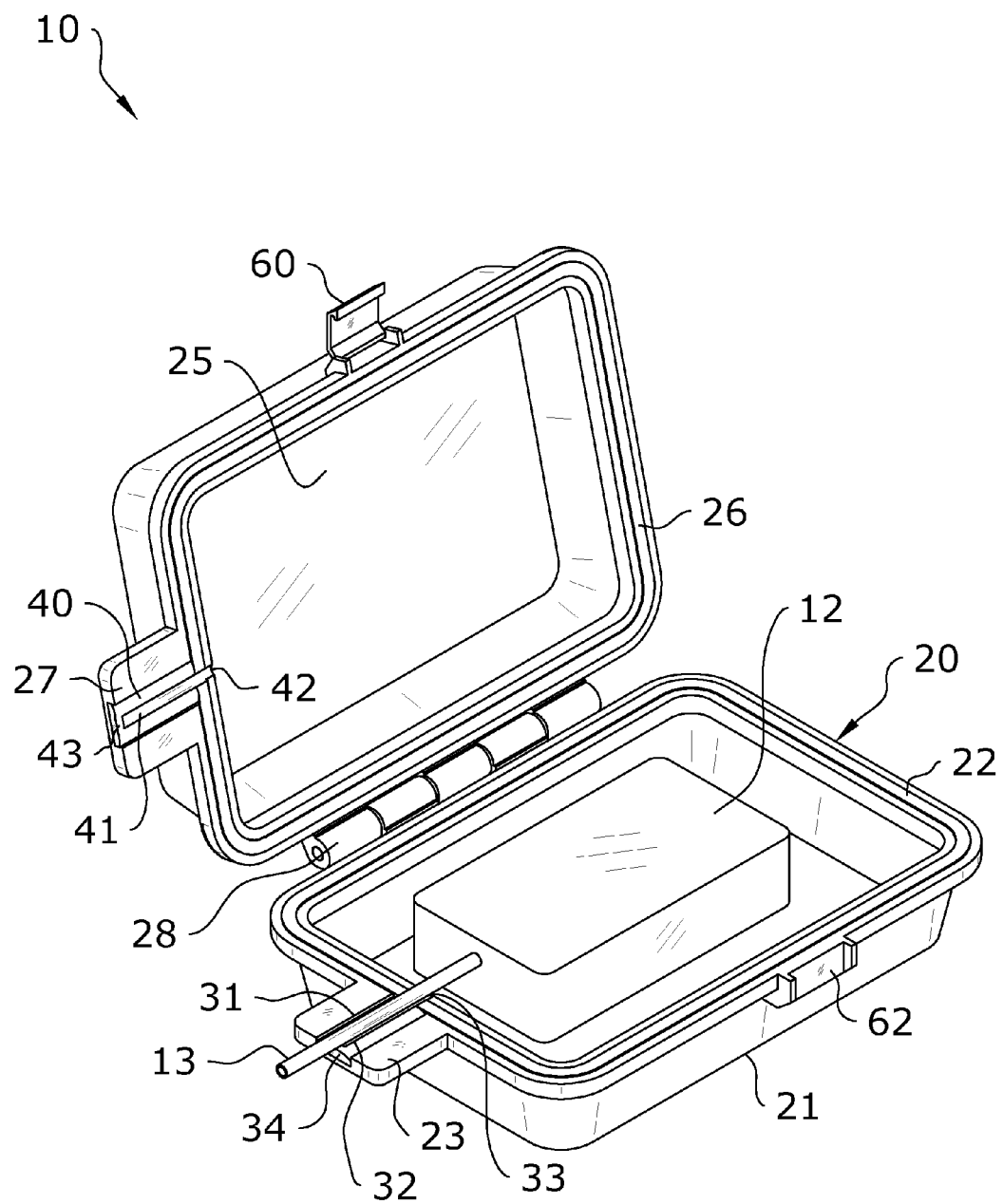
FIG. 3 is an upper perspective view of the fluidic device positioned within the case of the present invention.
Figure 4:
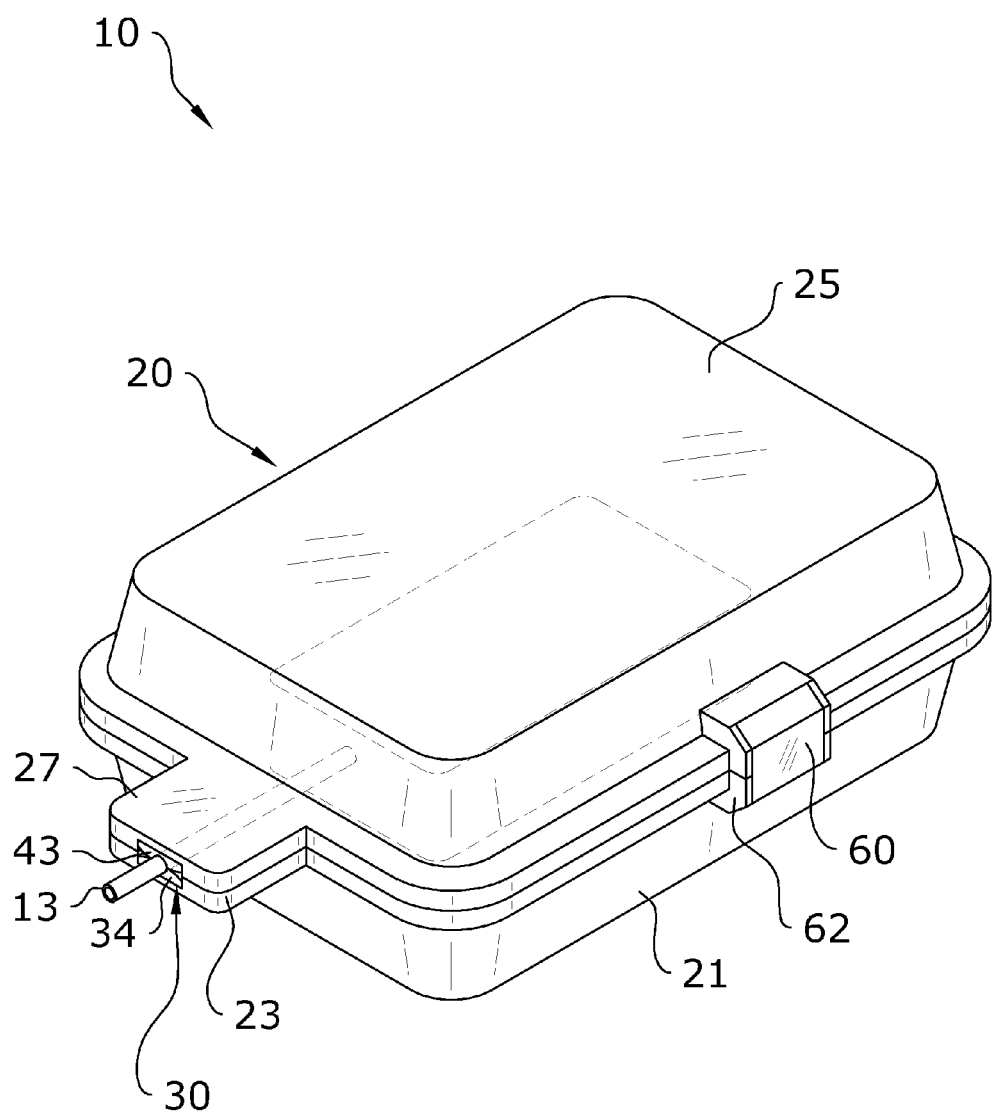
FIG. 4 is an upper perspective view illustrating a tube extending through the passage of the case of the present invention.
Figure 18:
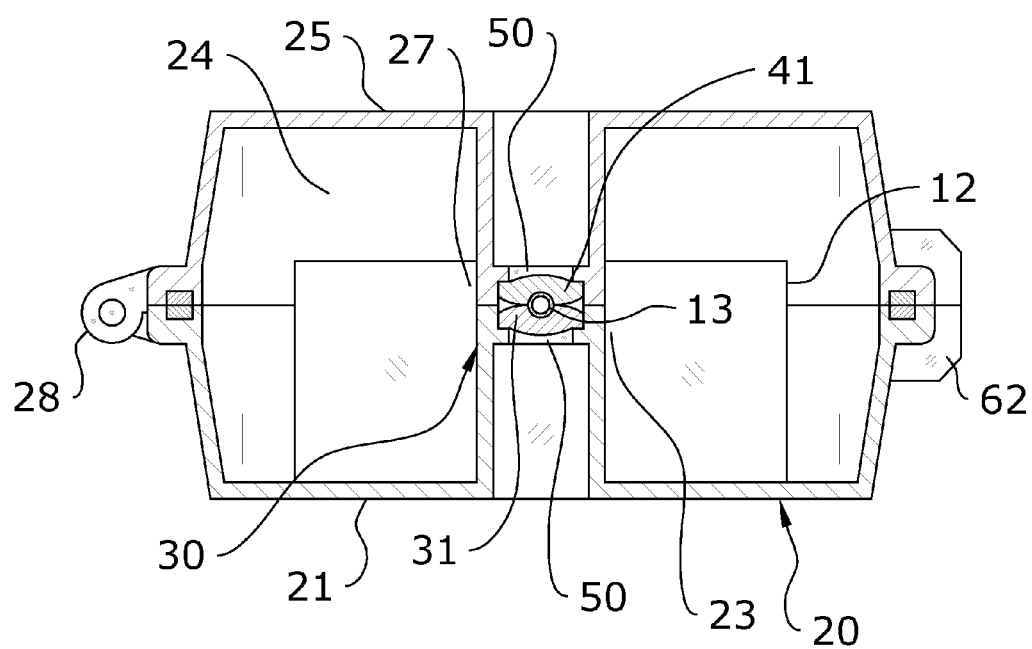
FIG. 18 is a sectional view taken along line 18-18 of FIG. 17.

As best shown in FIGS. 2, 3, and 18, the tube seal assembly 30 may comprise a first tube seal 31 positioned on the first portion 21 of the case 20 and a second tube seal 40 positioned on the second portion 25 of the case 20. Each tube seal 31, 40 generally comprises a sealing material such as rubber, with the first tube seal 31 adapted to press and seal against the second tube seal 40 when the case 20 is closed. The tube seals 31, 40 may be transparent or partially transparent in some embodiments. In some embodiments, the first tube seal 31 may be integrally formed with the first perimeter seal 22 and the second tube seal 40 may be integrally formed with the second perimeter seal 26.

The positioning of the tube seals 31, 40 within the case 20 may vary in different embodiments. Preferred embodiments will utilize a pair of mounts 23, 27 comprised of extended sections of the case 20 which include the tube seals 31, 40. As shown in FIG. 2, the first portion 21 of the case 20 will generally include a first mount 23 and the second portion 25 of the case 20 will generally include a second mount 27. FIGS. 1-9 and 11 illustrate an embodiment in which the mounts 23, 27 extend outwardly from the perimeter of the case 20. FIGS. 12-21 illustrate an embodiment in which the mounts 23, 27 extend inwardly from the perimeter of the case 20.

The tube seals 31, 40 are each generally comprised of a rectangular or similarly-shaped member with a channel 32, 41 formed in the member which extends perpendicularly with respect to the perimeter of the case 20. The material used in the tube seals 31, 40 may vary in different embodiments, but will preferably be resilient so as to bulge outward when the blocking portions 35, 44 are deformed around a tube 13.

The first tube seal 31 will generally include a first channel 32 and the second tube seal 40 will generally include a second channel 41 as best shown in FIG. 2. When the case 20 is closed, the first channel 32 and second channel 41 will combine to form a passage 48 through which the tube 13 of the fluidic device 12 may extend to exit the compartment 24 of the case 20.

To prevent ingress of fluids into the case 20 when no tube 13 is present, the first tube seal 31 will generally include a first blocking portion 35 and the second tube seal 40 will generally include a second blocking portion 44. The blocking portions 35, 44 will press and seal against each other when the case 20 is in its closed state to seal the passage 48 and prevent fluid escapement. Thus, the first blocking portion 35 will preferably be aligned with the second blocking portion 44 such that they contact each other when the case 20 is closed.

Each blocking portion 35, 44 is generally comprised of a flexible, resilient material such as rubber which extends across each respective channel 32, 41 of the tube seals 31, 40. The size, shape, and configuration of the blocking portions 35, 44 may vary in different embodiments so long as they act to seal the passage 48 when no tube 13 is present and the case 20 is closed.

When a tube 13 is installed in the case 20, the passage 48 is sealed by the exterior diameter of the tube 13 compressing material in the unblocked portion of the passage 48. Because the passage 48 is sealed against the tube 13 body, the blocking portions 35, 44 no longer must seal and can therefore tolerate significant deformation from deforming around the tube 13 body.

The blocking portions 35, 44 may be positioned differently in different embodiments of the present invention. FIGS. 2, 11, 12, and 13 illustrate alternate positioning of the blocking portions 35, 44. FIG. 2 illustrates an embodiment in which the first blocking portion 35 is positioned at the distal end 34 of the first channel 32 and the second blocking portion 44 is positioned at the distal end 43 of the second channel 41.

Figure 11:
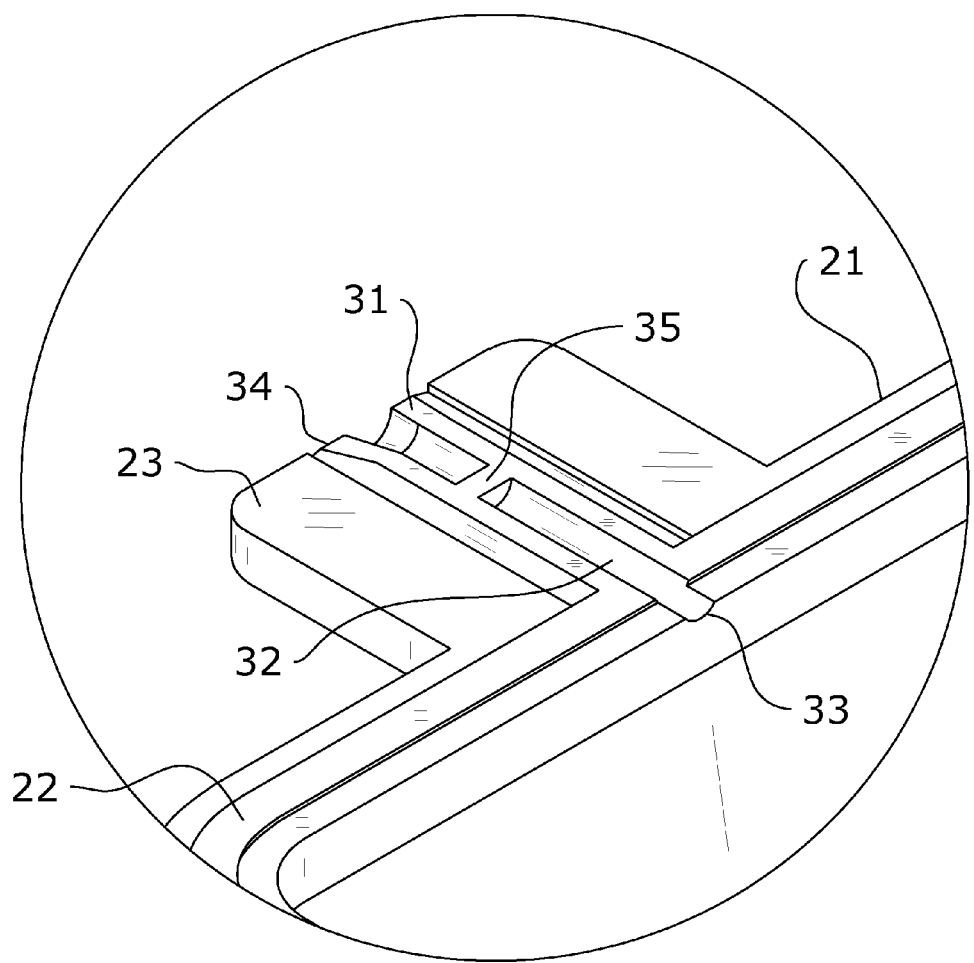
FIG. 11 is a close-up upper perspective view of a first embodiment of a tube seal of the present invention.
Figure 12:
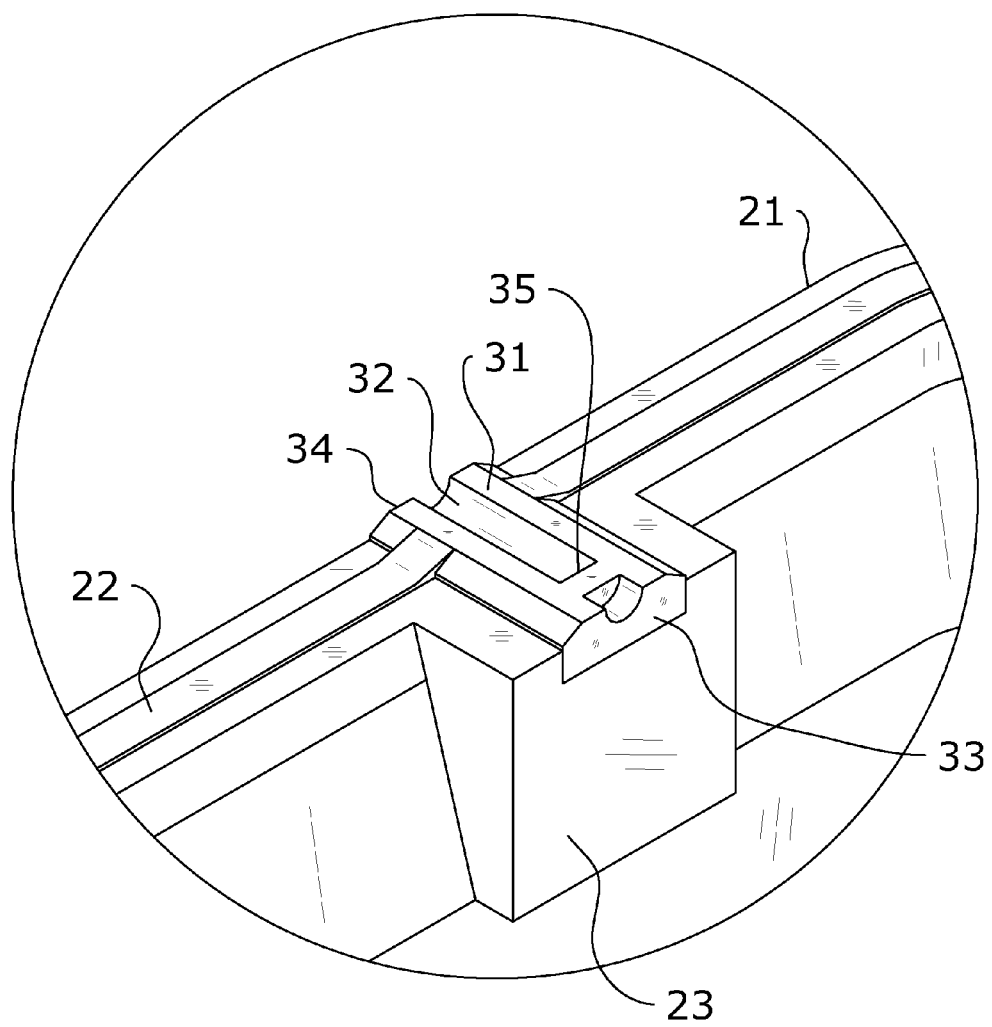
FIG. 12 is a close-up upper perspective view of a second embodiment of a tube seal of the present invention.
Figure 13:
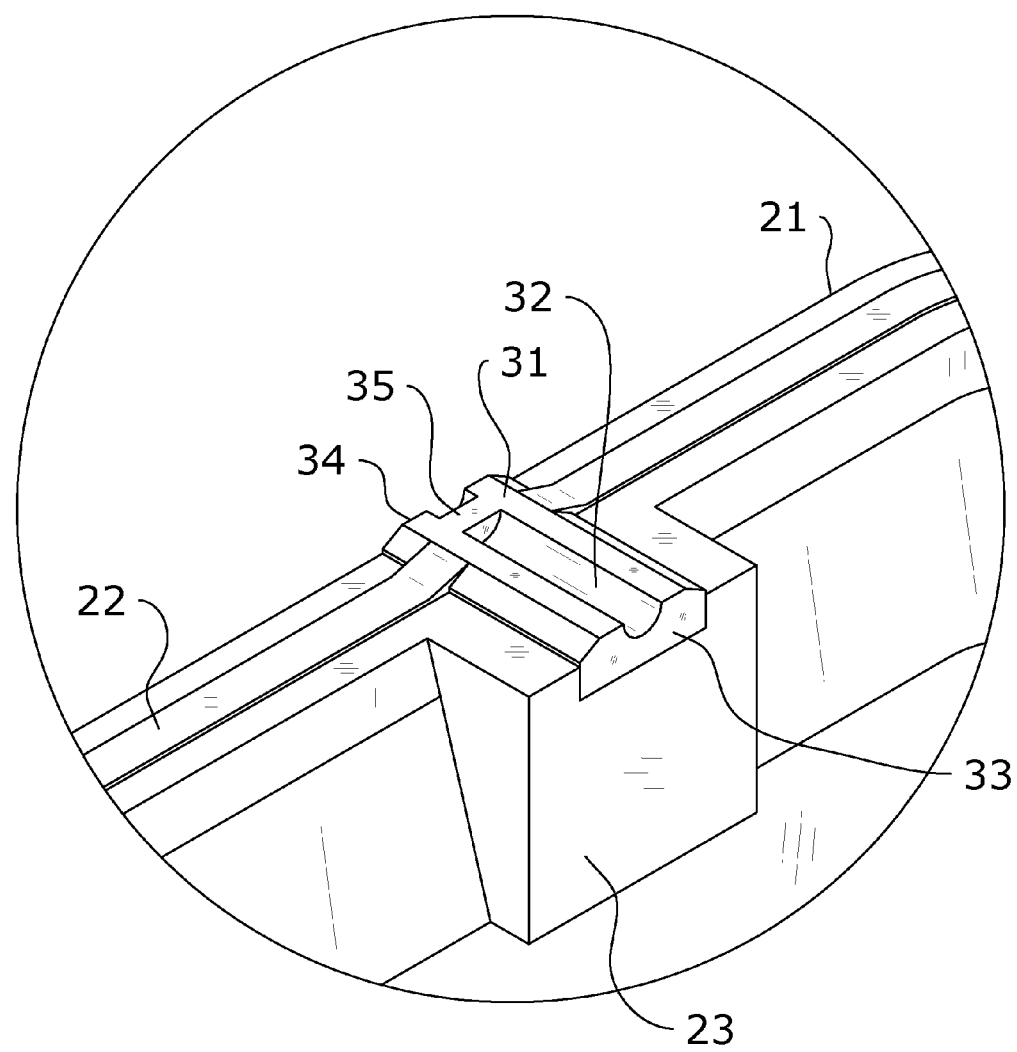
FIG. 13 is a close-up upper perspective view of a third embodiment of a tube seal of the present invention.

FIG. 11 illustrates an alternate embodiment in which the blocking portions 35, 44 are positioned at approximately 40% of the length between the distal ends 34, 43 and proximal ends 33, 42 of the respective channels 32, 41. FIG. 12 illustrates an embodiment in which the blocking portions 35, 44 are positioned adjacent to the proximal ends 33, 42 of the respective channels 32, 41. FIG. 13 illustrates an embodiment in which the blocking portions 35, 44 are positioned adjacent to the distal ends 34, 43 of the respective channels 32, 41.

Any configuration may be utilized, and it should be appreciated that the positioning of the blocking portions 35, 44 may vary widely between different embodiments. The scope of the present invention should not be construed as being limited by the exemplary figures. The blocking portions 35, 44 could be positioned at any position between and including the respective ends 33, 34, 42, 43 of the respective channels 32, 41.

The interior walls of the tubular channels 32, 41 of the tube seals 31, 40 may be round and smooth as best shown in FIGS. 11-13. While this configuration may work for most uses, it may also require precise tolerances on the tube seal 31, 40 outer diameters and on the tubular channel 32, 41 area of each seal 31, 40. Non-foam elastomers are similar to hydraulic fluid in that they are incompressible and when a seal is compressed the compressed material must bulge out somewhere else.

Figure 14:
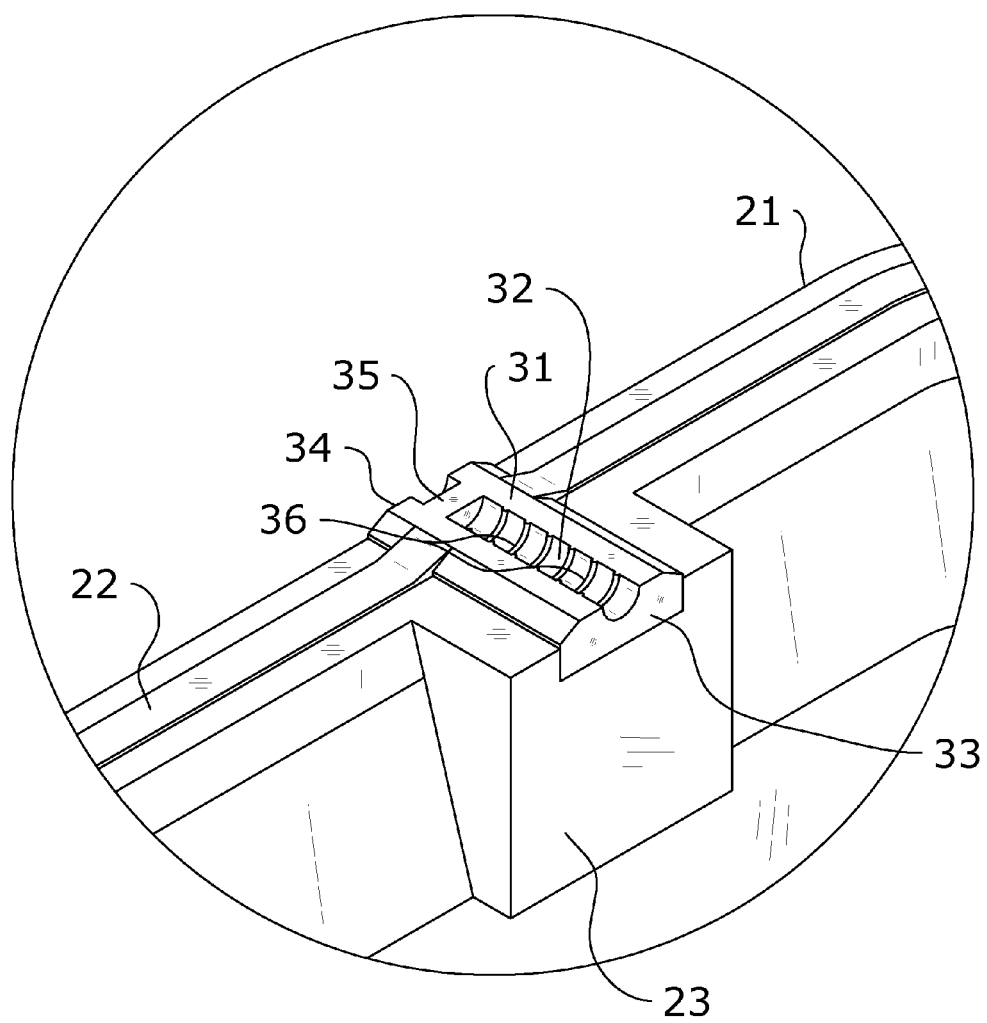
FIG. 14 is a close-up upper perspective view of a third embodiment of a tube seal of the present invention with ribs.
Figure 15:
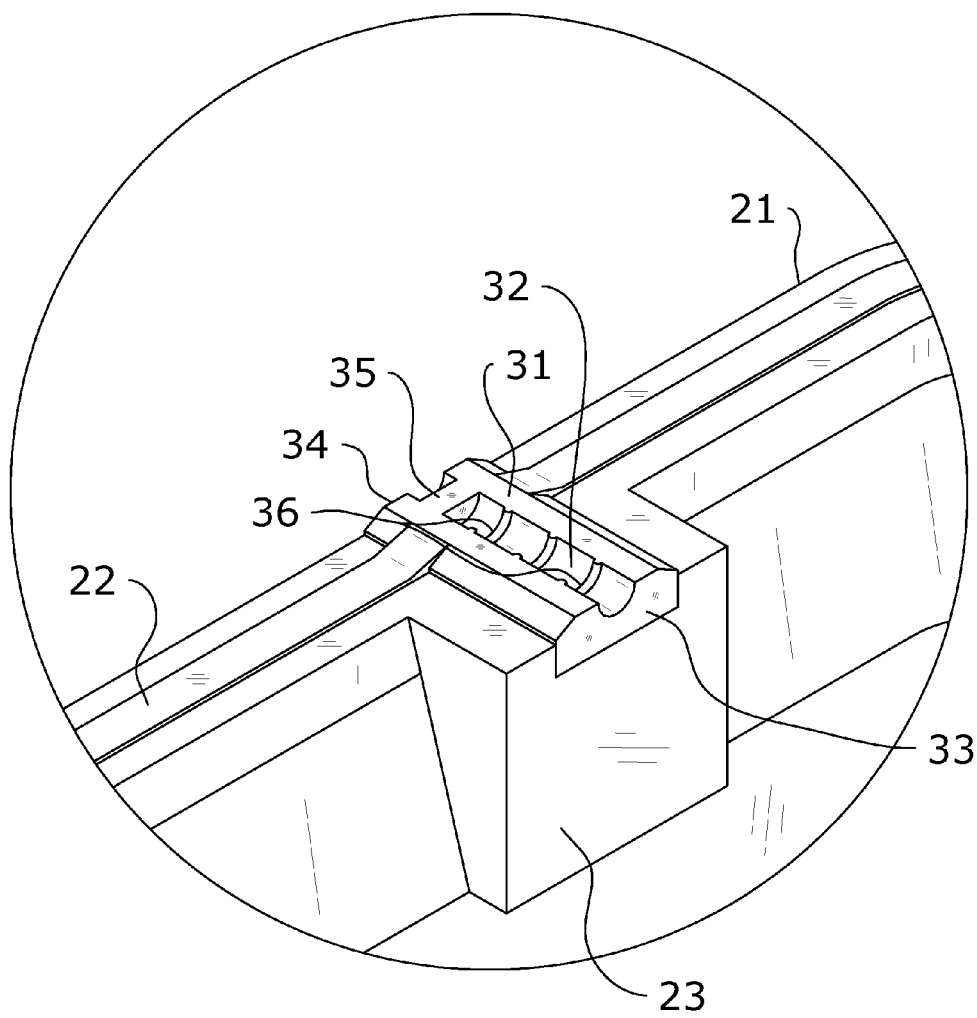
FIG. 15 is a close-up upper perspective of the third embodiment of the tube seal of the present invention with a second embodiment of ribs.

To alleviate this potential problem, some embodiments of the present invention will include a ribbed profile as best shown in FIGS. 14, 15, and 18. In such embodiments, first ribs 36 will be positioned within the first channel 32 and second ribs 45 will be positioned within the second channel 41. Each rib 36, 45 is generally comprised of a raised elongated portion extending within the inner circumference of the channels 32, 41.

FIG. 14 illustrates a first channel 32 having closely-spaced first ribs 36. When the tips of the ribs 36 are compressed by the tube 13, the seal material can bulge out into the spaces between the ribs 36. This will allow a lower closing force than if the entire main seal 31, 40 body had to be compressed to seal against the tube 13. FIG. 15 illustrates a first channel 32 having more space between the first ribs 36. This configuration will function similarly to the previously-described embodiment but with the added benefit of the redundancy provided by multiple independent sealing areas.

Figure 16:
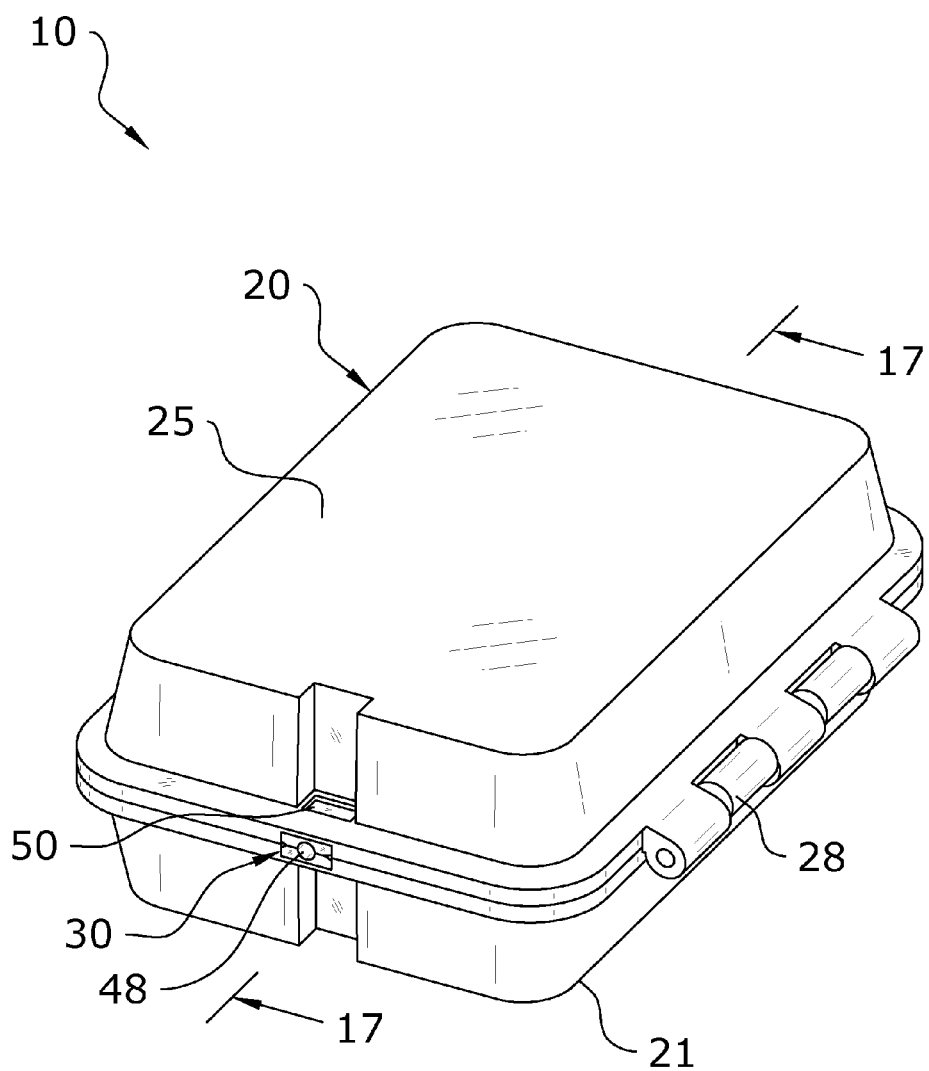
FIG. 16 is a side upper perspective view of the present invention with a displacement opening in the case.

FIG. 16 illustrates an embodiment in which the case includes a displacement opening 50 aligned with the tube seal assembly 30. This feature may be included in embodiments where the tube 13 wall is more flexible but not stiff enough to displace the blocking portions 35, 44 of the seals 31, 40 without collapsing the tube 13 wall itself. The displacement opening 50 allows the blocking portions 35, 44 to be displaced therein instead of simply compressing the material of the tube 13 to prevent free flow of fluid there through.

D. Operation of Preferred Embodiment

In use, the case 20 is first placed into its opened state by separating its first portion 21 from its second portion 25 to expose its compartment 24. The fluidic device 12 may then be positioned within the compartment 24 of the case 20 as shown in FIGS. 2 and 3. The fluidic device 12 may be secured in place within the compartment 24 through any methods or devices known to secure a device within a case 20.

The present invention may be utilized with any type of fluidic device 12 that includes a tube 13 or other conduit extending therefrom and which would benefit from being protected by a case 20. For example and without limitation, the fluidic device 12 could be comprised of an insulin pump, which generally utilizes a tubing system which extends from an insulin reservoir and interfaces with a patient's body.

Figure 5:
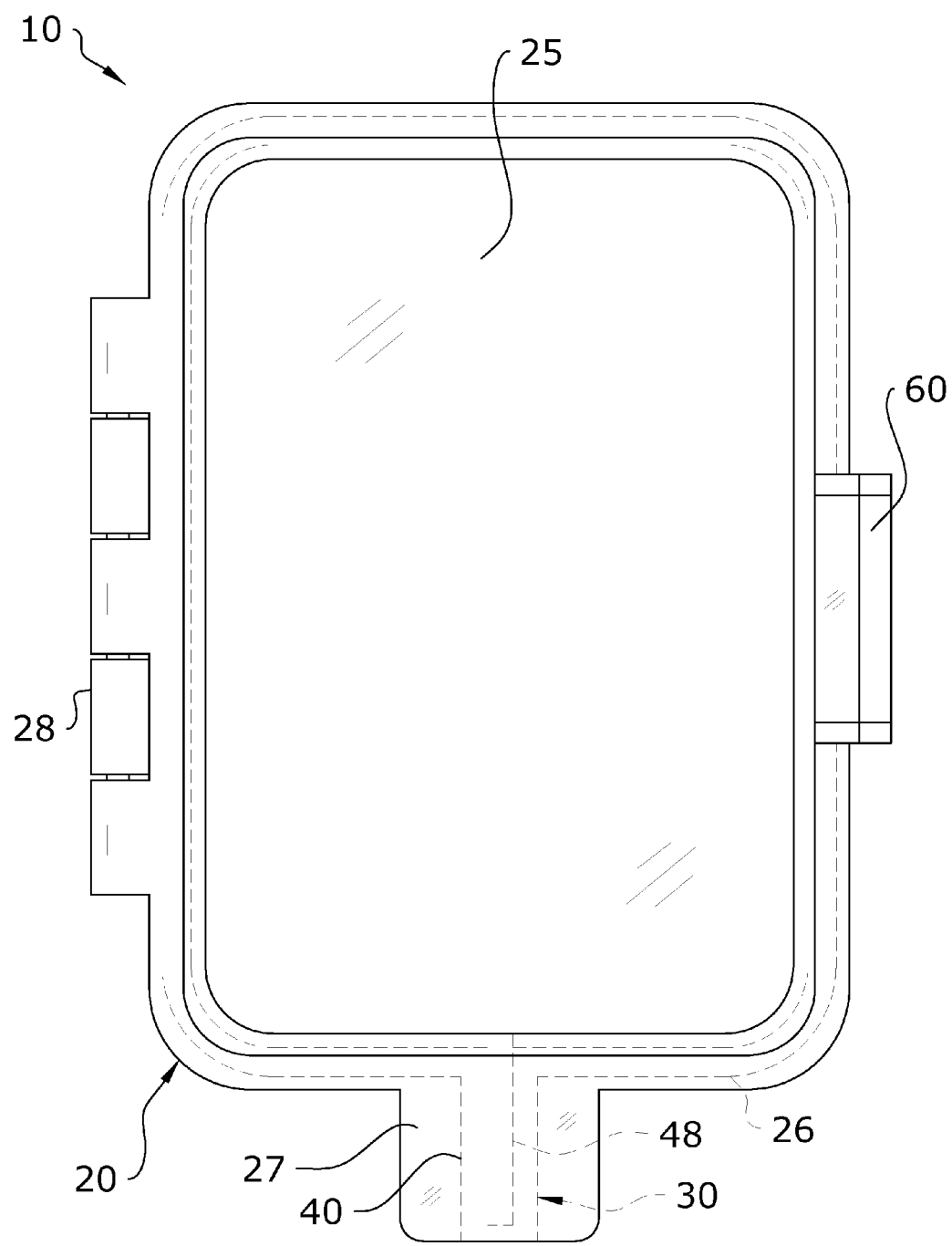
FIG. 5 is a top view of the case of the present invention in a closed position without a fluidic device positioned therein.

With the fluidic device 12 positioned within the compartment 24, the case 20 may be placed into its closed state to protect the fluidic device 12 as shown in FIG. 5. The tube 13 of the fluidic device 12, if present, will be positioned within the first channel 32 of the first tube seal 31 so as to extend out of the case 20 prior to its closing.

The first and second portions 21, 25 of the case 20 may then be closed together to encapsulate the fluidic device 12 within the compartment 24. When the case is in its closed state, the perimeter seals 22, 26 and/or perimeter engagement member 29 will act to seal the compartment 24 and prevent intrusion of fluids into the compartment 24 of the case 20 whether a tube 13 extends out of the compartment 24 or not. In some embodiments, the portions 21, 25 may be secured or locked to each other to prevent inadvertent opening of the case 20.

When closed, the first channel 32 of the first tube seal 31 and the second channel 41 of the second tube seal 40 will combine to form a passage 48 through which the tube 13, if present, extends out of the case 20. FIG. 5 best illustrates a tube 13 of a fluidic device 12 extending out of the compartment 24 of the case 20 through the passage 48.

Figure 9:
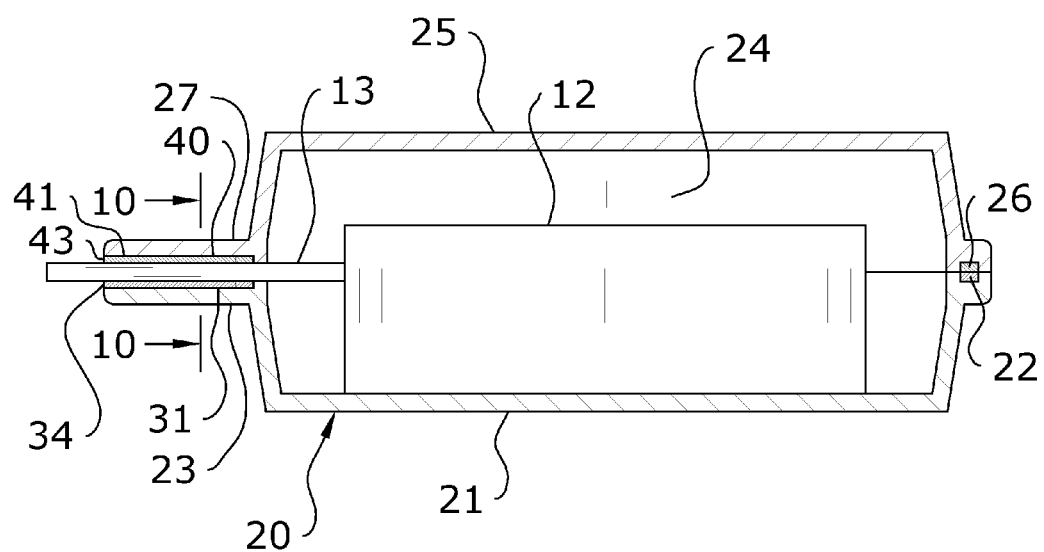
FIG. 9 is a side sectional view of the present invention with a fluidic device positioned within the container.
Figure 10A:
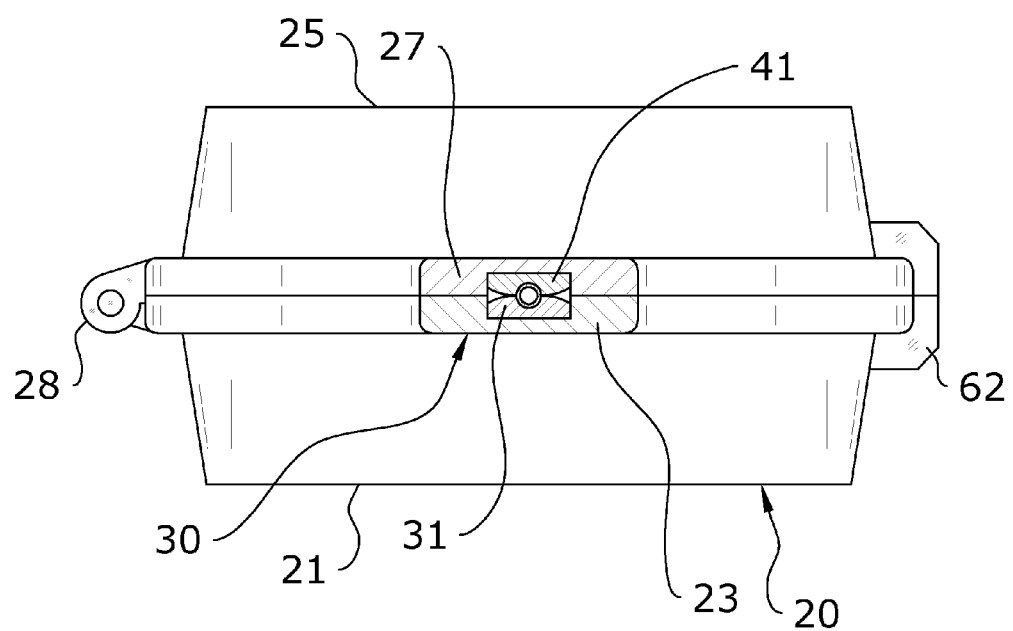
FIG. 10a is a frontal view illustrating the deformation of the tube seals around a tube of the present invention to seal the case when a tube is present taken along line 10-10 of FIG. 8.
Figure 10B:
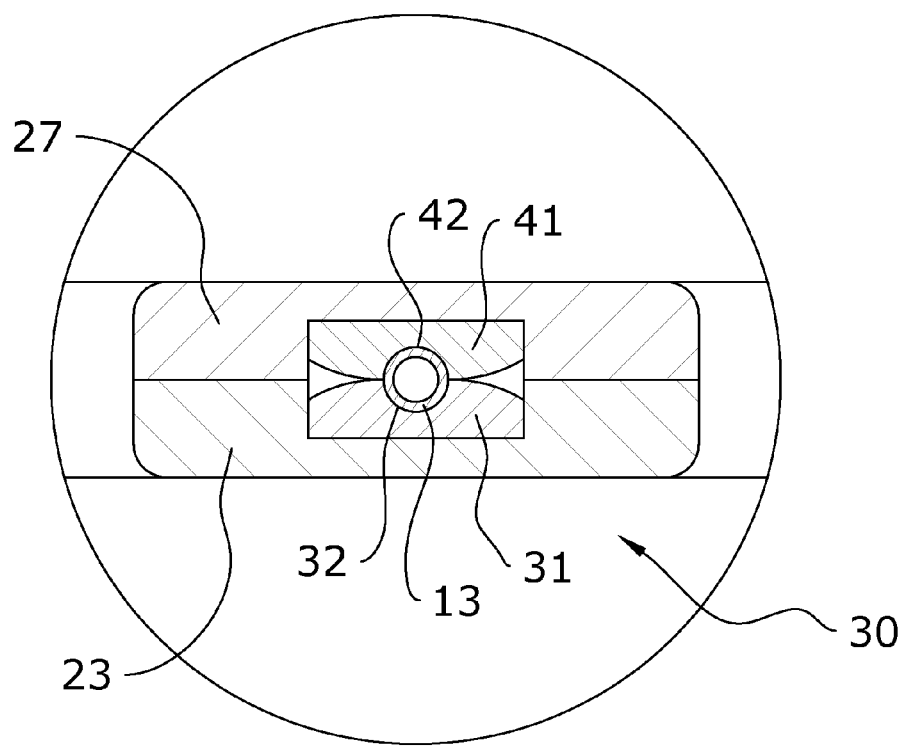
FIG. 10b is a close-up frontal view illustrating the deformation of the tube seals around a tube of the present invention to seal the case when a tube is present taken along line 10-10 of FIG. 8.

FIG. 9 shows a tube 13 extending through the passage 48 in an embodiment which omits blocking portions 35, 44. The tube seal assembly 30 will prevent leakage through the first and second tube seals 31, 40 pressing and sealing around the body of the tube 13 when the tube 13 is present. However, the passage 48 will remained open absent the tube 13, which may allow fluid intrusion when a tube 13 is not present in the passage 48.

Figure 17:
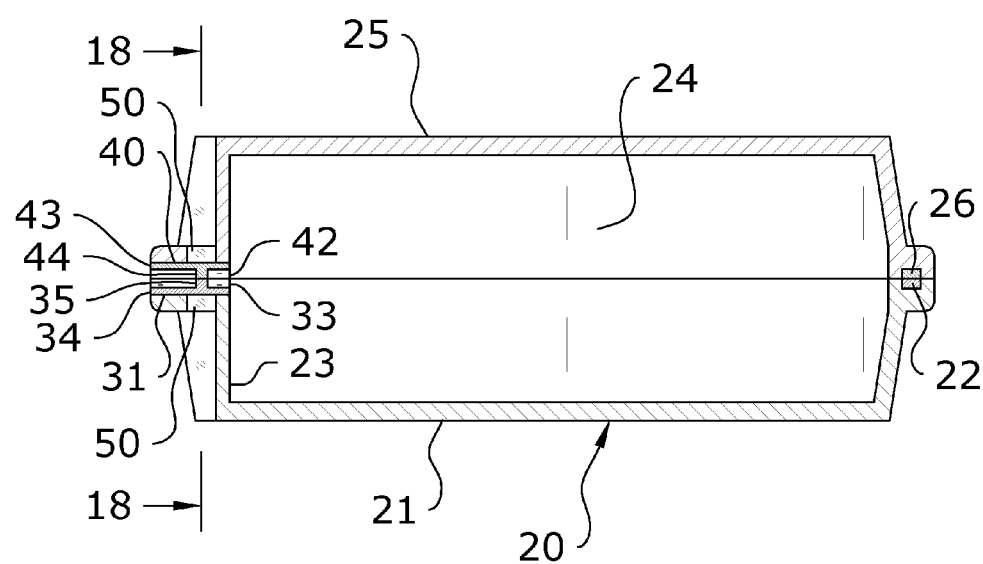
FIG. 17 is a sectional view taken along line 17-17 of FIG. 16.

To alleviate this potential problem, some embodiments of the present invention may utilize one or more blocking portions 35, 44. The blocking portions 35, 44 will act to close the passage 48 when a tube 13 is not present therein. FIG. 17 best illustrates the sealing of the passage 48 absent the presence of a tube 13 therein in such embodiments which utilize blocking portions 35, 44. When the case 20 is closed without a tube 13, the blocking portions 35, 44 will press against each other to close the passageway 48. This will seal the compartment 24 and prevent fluid leakage into or out of the compartment 24.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A tube passage sealer, comprising:

a case for containing a device therein, said case including a first portion and a second portion, wherein said case has an opened state wherein said first and second portions are relatively separated such than an interior of the case is open, and wherein said case has a closed state wherein said first and second portions are closed together such that said interior of said case is sealed from an outside environment and said device can be contained therein;

a first tube seal of flexible material extending through a first recess in said first portion, said first tube seal having a first channel extending therethough, and wherein said first tube seal includes a first blocking portion extending across and completely filling a portion said first channel;

a second tube seal of flexible material extending through a second recess in said second portion, said second tube seal having a second channel extending therethrough, and wherein said second tube seal includes a second blocking portion extending across and completely filling a portion of said second channel;

a first perimeter seal surrounding a perimeter of said first portion of said case and integrally formed with said first tube seal; and a second perimeter seal surrounding a perimeter of said second portion of said case and integrally formed with said second tube seal, wherein in said closed state said first and second portions of said case are aligned, said first and second tube seals are aligned and contact one another, said first and second blocking portions are aligned, said first and second perimeter seals are aligned and contact one another, and said first and second channels are aligned, and wherein in said closed state said aligned first and second channels combine to form a passage adapted to receive a tube extending from said device to said outside environment, wherein said first tube seal and said second tube seal are operable to seal around said tube when said case is in said closed state, wherein said first tube seal and said second tube seal are adapted to seal said passage when said case is in said closed position and said tube is not positioned therein due to said first and second blocking members filling and sealing said passage, and wherein said first blocking portion and said second blocking portion are adapted to deform around said tube and allow passage of said tube when said tube is positioned within said passage.

2. The tube passage sealer of claim 1, wherein said first blocking portion is adjacent to a distal end of said first tube seal with respect to said first portion of said case and wherein said second blocking portion is adjacent to a distal end of said second tube seal with respect to said second portion of said case.

3. The tube passage sealer of claim 1, wherein said first blocking portion is adjacent to a proximal end of said first tube seal with respect to said first portion of said case and wherein said second blocking portion is adjacent to a proximal end of said second tube seal with respect to said second portion of said case.

4. The tube passage sealer of claim 1, wherein said first blocking portion is positioned adjacent to a mid-point of said first tube seal and wherein said second blocking portion is positioned adjacent to a mid-point of said second tube seal.

5. The tube passage sealer of claim 1, wherein said first tube seal includes one or more first ribs.

6. The tube passage sealer of claim 5, wherein said second tube seal includes one or more second ribs.

7. The tube passage sealer of claim 1, wherein said case includes a first extending mount, wherein said first tube seal is positioned on said first extending mount.

8. The tube passage sealer of claim 7, wherein said case includes a second extending mount, wherein said second tube seal is positioned on said second extending mount.

9. The tube passage sealer of claim 8, wherein said first extending mount extends outwardly from a perimeter of said first portion of said case and said second extending mount extend outwardly from the perimeter of said second portion of said case.

10. The tube passage sealer of claim 8, wherein said first extending mount extends inwardly from a perimeter of said first portion of said case and said second extending mount extend inwardly from the perimeter of said second portion of said case.

11. The tube passage sealer of claim 1, wherein said first portion of said case includes a first displacement opening aligned with said first tube seal to allow said first tube seal to be displaced by said tube when said tube is positioned within said passage.

12. The tube passage sealer of claim 11, wherein said second portion of said case includes a second displacement opening aligned with said second tube seal to allow said second tube seal to be displaced by said tube when said tube is positioned within said passage.

* * * * *

UNITED STATES PATENT AND TRADEMARK OFFICE
CERTIFICATE OF CORRECTION

PATENT NO. : 9,629,954 B2
APPLICATION NO. : 14/704637
DATED : April 25, 2017
INVENTOR(S) : Mitchell et al.

Page 1 of 1

It is certified that error appears in the above-identified patent and that said Letters Patent is hereby corrected as shown below:

In the Claims

Column 9, Line 6, "than" should read "that"
Column 9, Line 14, "therethough" should read "therethrough"
Column 9, Line 17, "filling a portion said first channel" should read "filling a portion of said first channel"

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*